United States Patent [19]

Calvet et al.

[11] Patent Number: 4,929,614
[45] Date of Patent: May 29, 1990

[54] BENZODIAZEPINES, PROCESS AND INTERMEDIATES FOR THE PREPARATION THEREOF AND THEIR APPLICATION IN THERAPY

[75] Inventors: Alain P. Calvet, L'Hay-les-Roses; Jean-Louis Junien, Sevres; Ives R. Pascal, Rueil Malmaison; Xavier B. Pascaud, Paris; François J. Roman, Courbevoie, all of France

[73] Assignee: Jouveinal S.A., Paris, France

[21] Appl. No.: 337,940

[22] Filed: Apr. 14, 1989

[30] Foreign Application Priority Data

Apr. 25, 1988 [FR] France .................. 88 05443

[51] Int. Cl.$^5$ ............. A61K 31/55; C07D 487/04; C07D 471/04
[52] U.S. Cl. .................... 514/214; 540/496
[58] Field of Search ............. 540/496; 514/214

[56] References Cited
FOREIGN PATENT DOCUMENTS 167919 1/1986 European Pat. Off. ......... 540/504

*Primary Examiner*—Robert T. Bond
*Attorney, Agent, or Firm*—Cushman, Darby & Cushman

[57] ABSTRACT

Benzodiazepines of formula

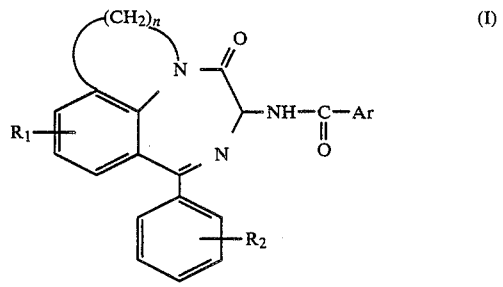

in which $R_1$ is H of halogen, $R_2$ is H or halogen, Ar is indolyl, phenyl, naphthyl, indolyl monosubstituted with a halogen or with a methoxy or phenyl mono-, di- or trisubstituted with a halogen or with a methoxy or with a trifluoromethyl group, and n is 2 or 3; and their optical isomers.

10 Claims, No Drawings

BENZODIAZEPINES, PROCESS AND INTERMEDIATES FOR THE PREPARATION THEREOF AND THEIR APPLICATION IN THERAPY

The present invention relates to benzodiazepines, to a process and intermediates for the preparation thereof and to their application in therapy.

Cholecystokinin, abbreviated below to CCK, is a peptide containing thirty-three amino acids in the form originally isolated. However, active forms containing thirty-nine, twelve and eight amino acids circulate in the body. The form containing the eight amino acids of the carboxy-terminal end of the peptide is the shortest amino acid arrangement displaying activity. It is designated below by the abbreviations CCK-8, CCK-8 $SO_4$ or sulphated CCK-8; the latter two abbreviations signify that the phenol group of the tyrosine at position 27 of the cholecystokinin is esterified by an —$SO_3H$ group, as is the case in the natural form.

Benzodiazepines which are cholecystokinin antagonists which bind specifically to receptors for this peptide, thereby enabling their use to be envisaged in the treatment of disorders of the central nervous system, the stomach, the intestine, the pancreas or the gallbladder, and of other CCK-dependent disorders, have already been described in European Patent 0 167 919. Among the vast number of benzodiazepines included in European Patent 167,919, (+/—)-N-(2,3-dihydro-1-methyl-2-oxo-5-phenyl-3-(1H-benzodiazepin-1,4-yl)-2-(1H)-indolecarboxamide, hereinafter designated compounds IIa, was the one chosen by the patentee with a view to being developed at the industrial scale (Pharma Project, 12th Jan. 1987).

In point of fact, benzodiazepines have now been found which, while displaying activities substantially equal to those of the most active compounds of the above-mentioned European Patent, and in particular those of the compound (IIa), are distinctly less toxic, so that their therapeutic index is better. Moreover, the ratio of the 50% inhibitory concentration ($IC_{50}$) for the CCK receptors of guinea-pig brain to the $IC_{50}$ for the receptors of rat pancreas favors a peripheral activity, thereby giving rise to the hope of better selectivity in the treatment of conditions dependent on peripheral control, and hence of medicinal products possessing few side effects, if any.

The subject of the invention is hence benzodiazepines of formula (I):

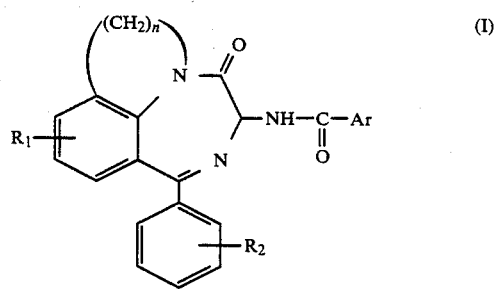

in which $R_1$ is H or halogen, $R_2$ is H or halogen, Ar is indolyl, phenyl, naphthyl, indolyl monosubstituted with a halogen or with a methoxy or phenyl mono-, di- or trisubstituted with a halogen, with a methoxy or with a trifluoromethyl group, and n is 2 or 3; and their optical isomers.

Among these new benzodiazepines, those in which $R_1$ is in the para-position with respect to the nitrogen atom common to the diazepine ring and to the other nitrogen heterocycle fused to the diazepine ring are most especially preferred. Preferably also, $R_1$ is chlorine. The compounds in which $R_2$ is at the ortho-position with respect to the carbon atom linking the phenyl ring to the diazepine ring are also preferred, fluorine being the preferred meaning for $R_2$. Preferred compounds include those for which Ar is 2-indolyl. Generally speaking, the benzodiazepines of formula (I) in which the asymmetric carbon atom at the alpha-position with respect to the carbonyl of the diazepine ring possesses the S absolute configuration, this configuration being defined according to the nomenclature of Cahn, Ingold and Prelog.

The invention also relates to a process for preparing benzodiazepines of formula (I) which consists in reacting (a) a racemic amine of formula (V):

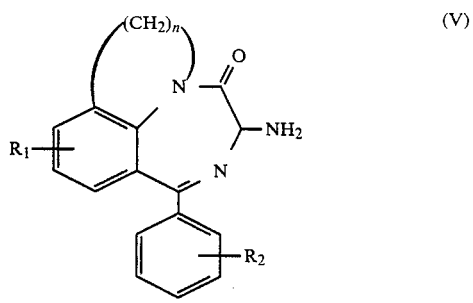

with a carboxylic acid derivative of formula Ar—CO—X, in which Ar has the meaning stated above and X is a halogen, an azido (—$N_3$) group, a 1-imidazolyl group, a group —O—CO—$R_3$, it being possible for $R_3$ to be, besides preferably Ar, a hindered alkyl radical containing from three to six carbon atoms, or an aryl radical more hindered than the radical Ar, preferably substituted with one or more halogens, or a group —$OR_4$, $R_4$ being an aromatic group containing one or two rings and substituted with one or more nitro or halogen radicals, to obtain a racemic compound of formula (I).

(b) An optically active amine of formula V, in the same manner as in paragraph (a), to obtain an optically active compound of formula (I).

It is possible, in particular, to work in the following manner: a compound of formula (V) is dissolved in 5 to 50 volumes of an anhydrous or hydrated organic solvent such as, for example, a chlorinated hydrocarbon such as dichloromethane or chloroform, a linear or cyclic ether such as 1,2-dimethoxyethane, tetrahydrofuran or dioxan, an aprotic polar solvent such as pyridine, dimethyl sulphoxide or dimethylformamide, or any other solvent in which it is appropriate to form a condensation reaction, or alternatively a suitable mixture of two or more of these solvents, and one to two equivalents of an acylating agent of formula Ar—CO—X, in which Ar has the meaning defined above and X is:

a halogen, preferably a chlorine,
an azido (—$N_3$) group
a 1-imidazolyl group a group of formula —O—CO—Ar, in which Ar has the meaning defined above, a group of formula —O—CO—R$_3$, in which R$_3$, has the meaning stated above, preferred groups R$_3$ being tert-butyl or 2,4,6-trichlorobenzoyl, a group of formula —O—R$_4$ in which R$_4$ has the meaning stated above, preferred groups R$_4$ being paranitrophenyl, 2,4-dinitrophenyl, pentachlorophenyl, pentafluorophenyl and 1-benzotriazolyl; in the latter case, the reagent may be prepared by reaction of the carboxylic acid ArCOOH (Ar having the meaning defined above) and 1-hydroxybenzotriazole in the presence of a carbodiimide such as, for example, dicyclohexylcarbodiimide or diisopropylcarbodiimide.

The same quantity of an inorganic or organic base such as an aliphatic amine, preferably triethylamine, is then added, and the mixture is stirred at a temperature between −20° C. and the boiling point of the mixture, for a period of between ten minutes and several hours, a period of thirty minutes to one hour generally being sufficient to ensure completion of the reaction. The reaction medium, optionally diluted with one of the solvents mentioned above, is then treated successively with a dilute solution of an inorganic acid such as, for example, a halogen hydracid or sulphuric acid, preferably approximately decinormal hydrochloric acid, then with saturated sodium bicarbonate solution and then with water. After evaporation of the solvent, the product is generally purified by chromatography on a silica column (flash chromatography) or by high pressure liquid chromatography (HPLC) and then, where appropriate, by recrystallization.

Another possibility consists in using as an acylating reagent a mixture of the carboxylic acid ArCO—X and a carbodiimide, preferably dicyclohexylcarbodiimide or diisopropylcarbodiimide.

Any other known process for the in situ formation of a reagent ArCO—X employed for forming an amide group is also suitable, and especially the processes using 2-ethoxy-1-ethyloxycarbonyl-1,2-dihydroquinoline (EEDQ, The peptides Gross et Meienhofer, vol. 1, Academic Press, 1979, p. 358), the so-called Woodward reagent (Woodward reagent K, The Peptides, Gross et Meienhofer, vol. 1, Academic Press, 1979, p. 122) or the so-called Castro reagent [(1-benzotriazol-1-yl-oxy)-tris-(dimethylamino)-phosphonium hexafluorophosphate] (J. Chem. Soc. Perkin Trans. 1, 1987, 1915–1919).

The amine of formula V may be prepared by aminating, at the alpha position with respect to the carbonyl, a 1,4-benzodiazepinone of formula (III):

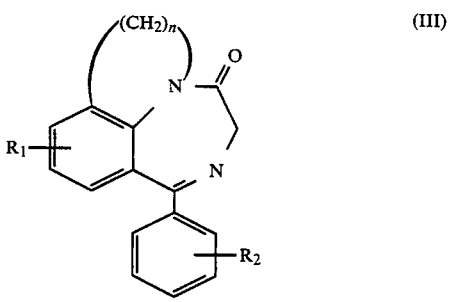

with a hydroxylamine derivative or with chloramine. It is also possible to aminate the 1,4-benzodiazepinone of formula (III) in two stages, the first stage consisting in reacting it with an oximation reagent of formula R$_5$—(N═O)$_m$, in which R$_5$ is lower alkoxy or chlorine when m is equal to 1 and is an additional bond between the nitrogen atoms when m is equal to 2, to obtain the oxime of formula (IV):

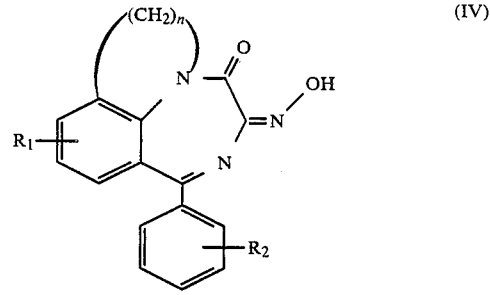

which is isolated, and the second stage consisting in reducing the oxime catalytically with hydrogen in the presence of a reduction catalyst or by reaction with zinc in the presence of acetic acid or with stannous chloride in the presence of hydrochloric acid, to obtain the amino derivative of formula V.

The amine of formula (V) can also be prepared by reacting a 1,4-benzodiazepinone of formula (III) in a basic medium with a reagent capable of introducing an azide group onto a carbanion to obtain an azide of formula (VI):

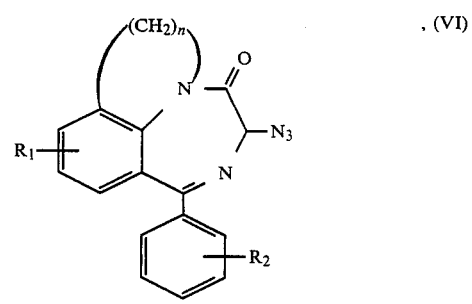

which is isolated, and then reducing the azide of formula (VI) with a reducing agent.

A compound of formula (III) is prepared by the process described by Hester J. B. et al., (J. Med. Chem.; 13; 827; 1970).

To prepare a compound of formula (V) in a single stage from a compound of formula (III), the following procedure is adopted:

A compound of formula (III) is dissolved in 10 to 100 volumes of an anhydrous organic solvent such as, for example, an aromatic hydrocarbon or a linear or cyclic ether such as, for example, tetrahydrofuran, or in an aprotic polar solvent such as dimethylformamide, hexamethylphosphorotriamide, dimethylsulphoxide, N-methylpyrrolidone or sulpholane (tetramethylene sulphone), or alternatively in a mixture of these solvents. The solution is maintained at a temperature of between −50° and 0° C., and 2 to 4 equivalents of a basic agent capable of displacing the proton at the α position with respect to the carbonyl group of the diazepine ring such as, for example, an alkali metal lower alcoholate, preferably potassium tert-butylate or tert-amylate, are added. The mixture is stirred for a period of between 10 and 60 minutes, and 3 to 20 equivalents of an amination reagent such as, for example, a hydroxylamine derivative, O-(2,4-dinitrophenyl)-hydroxylamine or O-(diphenylphosphinyl)-hydroxylamine or O-(2,4,6-trimethylphenylsulphonyl)-hydroxylamine or chloramine, are added thereto, and the mixture is then stirred for a period of between 10 and 60 minutes. The reaction medium is then concentrated, the salts present in the medium are filtered off, the medium is optionally diluted with water and the product extracted with a water-immicible organic solvent and, after evaporation of the solvent, the product is generally purified by chromatography on a silica column (flash chromatography) or by high pressure liquid chromatography (HPLC) and then, if appropriate, by recrystallization.

To prepare a compound of formula (V) in two stages, compound of formula (III), isolating an intermediate compound of formula (IV) containing an oxime group, the following procedure is adopted (preferred procedure):

A compound of formula (III) is dissolved in 10 to 100 volumes of an anhydrous organic solvent such as, for example, an aromatic hydrocarbon or a linear or cyclic ether such as, for example, tetrahydrofuran, or in an aprotic polar solvent such as dimethylformamide, hexamethylphosphorotriamide, dimethylsulfoxide, N-methylpyrrolidone or sulpholane, or alternatively in the mixture of these solvents. The solution is maintained at a temperature of between $-50°$ and $0°$ C., and 2 to 4 equivalents of a basic agent capable of displacing the proton at the alpha position with respect to the C=O, such as, for example, an alkali metal lower alcoholate, preferably potassium tert-butylate or tert-amylate, are added. The mixture is stirred for a period of between 10 and 16 minutes, and 3 to 20 equivalents of a lower alkyl nitrite, preferably isoamyl nitrite or nitrosyl chloride (NOCl) or alternatively nitrogen tetroxyde ($N_2O_4$) are added thereto, and the mixture is allowed to return to room temperature and then stirred for a period of between 10 and 60 minutes. The reaction medium is then neutralized by adding a ten-fold diluted solution of acetic acid and the product is extracted in one or more portions with a water-immicible organic solvent such as, for example, an aliphatic or aromatic hydrocarbon, a halogenated hydrocarbon, an ether or an ester of a lower alcohol with a lower carboxylic acid. After evaporation of the solvent, the product is then purified by chromatography on a silica column (flash chromatography) or by high pressure chromatography (HPLC) and then, where appropriate, by recrystallization.

The intermediate compound of formula (IV) is then converted to the amino compound of formula (V) in the following manner:

A compound of formula (IV) is suspended in 5 to 100 volumes of an organic solvent such as, for example, an lower aliphatic alcohol or an ester of a lower aliphatic alcohol with a lower carboxylic acid, in the presence of a hydrogenation catalyst such as, for example, Raney nickel, rhodium on charcoal or ruthenium on charcoal, which is the reagent generally preferred. The suspension is stirred under a hydrogen atmosphere at a pressure of between atmospheric pressure and 30 atmospheres for a period of between 1 and 50 hours at a temperature of between $0°$ C. and $80°$ C.; a pressure slightly above atmospheric pressure, a temperature of approximately $70°$ C. and a stirring time of 2 hours generally being sufficient to ensure complete reaction. The reaction medium is then filtered and the catalyst washed several times with a solvent of the same type as that mentioned above. After evaporation of the solvent, the product is generally purified by chromatography on a silica column (flash chromatography) or by high pressure liquid chromatography (HPLC) and then, where appropriate, by recrystallization. It is also possible to form the reduction chemically (in a stoichiometric manner) instead of catalytically, by treating the compound of formula (IV) with a reducing agent such as, for example, zinc in acetic acid or stannous chloride in hydrochloric acid or alternatively nickel boride (reagent prepared by the action of sodium borohydride on divalent nickel chloride).

To prepare a compound of formula (V) in two stages from a compound of formula (III), isolating an intermediate compound of formula (VI) containing an azide group, the procedure is as follows:

A compound of formula (III) is dissolved in 5 to 100 volumes of an anhydrous organic solvent such as, for example, an aromatic hydrocarbon or a linear or cyclic ether such as, for example, tetrahydrofuran, or in a polyether (solvent of the so-called glyme series), or in an aprotic polar solvent such as dimethylformamide, hexamethylphosphotriamide, dimethylsulphoxide, N-methylpyrrolidone or sulpholane, or alternatively in a mixture of these solvents. The solution is maintained at a temperature of between $-50°$ C. and room temperature, and 1 to 4 equivalents of a basic agent capable of displacing the proton at the alpha position of the CO of a compound of formula (III), such as, for example, an alkali metal lower alcoholate, preferably potassium tert-butylate or tert-amylate, butyl lithium, sodium hydride or sodium amide, are added. The mixture is stirred for a period of between 10 minutes and 6 hours, and 1 to 5 equivalents of a reagent capable of introducing an azide group onto a carbanion are added thereto, the preferred reagent being tosyl azide, and the mixture is allowed, where appropriate, to return to room temperature and then stirred for a period of between 10 minutes and 5 hours at a temperature between room temperature and the refluxing temperature of the mixture. The salts which are present in the reaction medium are then, where appropriate, filtered off, the reaction medium is then neutralized by adding a ten-fold diluted solution of acetic acid and the product is extracted in one or more portions with a water-immiscible organic solvent such as, for example, an aliphatic or aromatic hydrocarbon, a halogenated hydrocarbon, an ether or an ester of a lower alcohol with a lower carboxylic acid; the organic phase is then washed, where appropriate, with a dilute solution of an inorganic base or acid and then with water. After evaporation of the solvent, the product is generally purified by chromatography on a silica column (flash chromatography) or by high pressure liquid chromatography (HPLC) and then, where appropriate, by recrystallization.

The intermediate compound of formula (VI) is then converted to the amino compound of formula (V) in the following manner:

A compound of formula (VI) is suspended in 5 to 100 volumes of an organic solvent such as, for example, a lower aliphatic alcohol, an ester of a lower aliphatic alcohol with a lower carboxylic acid, an aromatic solvent such as, for example, benzene, toluene or pyridine, or water or alternatively a mixture of these solvents, and 1 to 10 equivalents of a reducing agent, such as, for example, vanadium (II) chloride ($VCl_2$) in aqueous solution, sodium borohydride (in the presence of methanol), hydrogen sulphide or Raney nickel are added thereto. The reaction medium is stirred at a temperature of between room temperature and the refluxing temperature of the mixture for a sufficiently long period to ensure completion of the reaction (depending on the nature of the reducing agent used, this period, which is determined by thin-layer chromatography, can vary from 10 minutes to several hours), and is then, where appropriate, cooled, filtered to remove the precipitate which may be present, neutralized and diluted, the solvent is removed by distillation under reduced pressure and the product is then purified by chromatography on a silica column (flash chromatography) or by high-pressure liquid chromatography (HPLC) and then, where appropriate, by recrystallization.

It is also possible to form this reduction catalytically instead of stoichiometrically, by treating the compound of formula (VI) with a reducing agent in the presence of a reduction catalyst such as, for example, ammonium formate in the presence of palladium on charcoal or hydrogen (under a pressure of between 1 and 5 atmospheres) in the presence of palladium deposited on calcium carbonate (so-called Lindlar catalyst). After filtration of the catalyst, the aminated product of formula (V) is isolated in a manner similar to that described above.

A scheme illustrating the process according to the invention is given below.

SYNTHESIS SCHEME

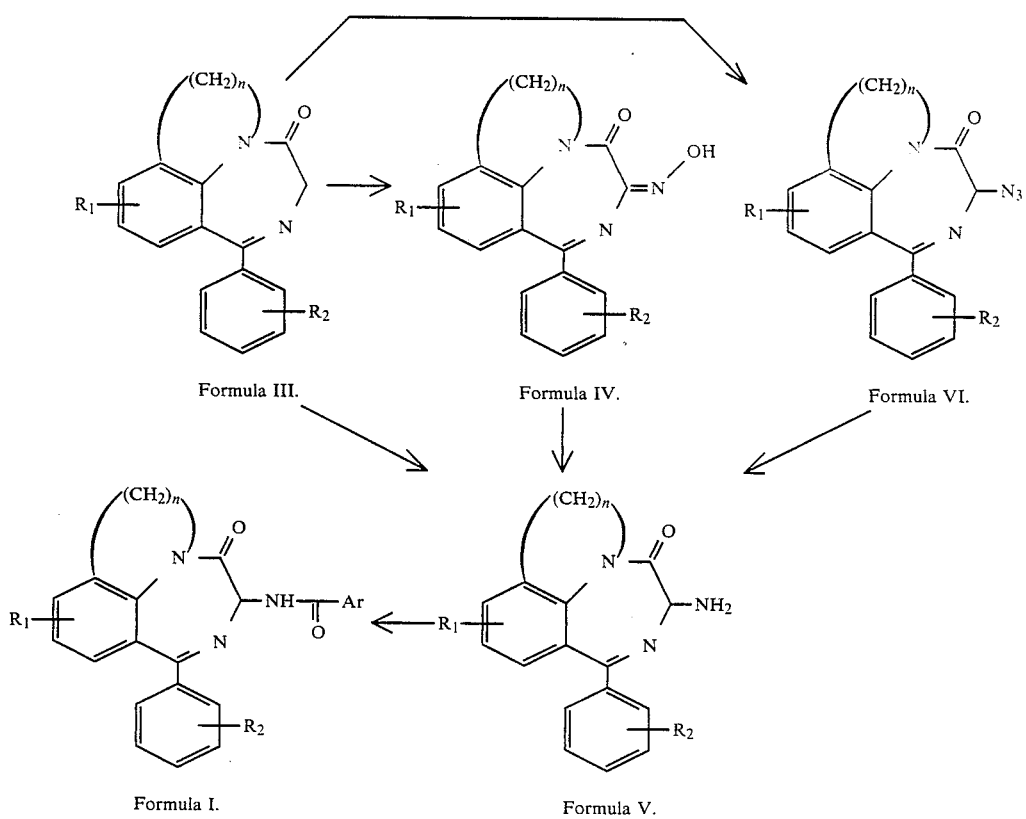

SEPARATION OF ISOMERS

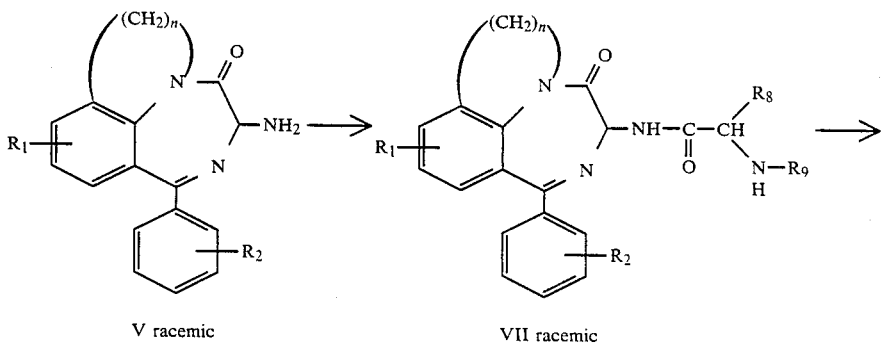

-continued
SEPARATION OF ISOMERS

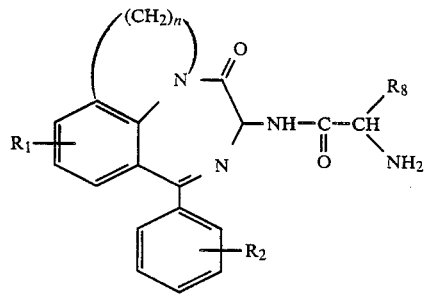

VIII racemic
followed by separation
into (+)-VIII and (−)-VIII

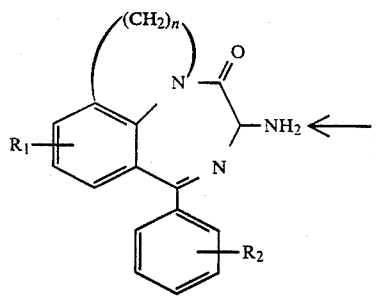 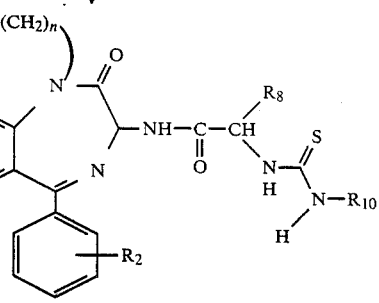

V optically active    IX optically pure

To prepare an optically active compound of formula I, the procedure is the same as above, starting with an optically active benzodiazepine of formula V, prepared in the following manner.

A racemic benzodiazepine of formula (V) is condensed with a molecule derived from an optically active amino acid, natural or otherwise, belonging to the D series or the L series, of formula (X):

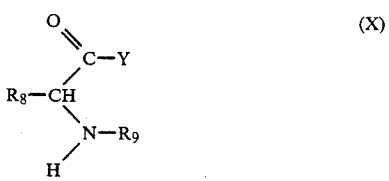

Y being a hydroxy group, an azido (—$N_3$) group, a 1-imidazolyl group, a group —O—CO—$R_3$, it being possible for $R_3$ to be a branched alkyl radical containing from three to six carbon atoms, a hindered aryl group, preferably substituted with one or more halogens, or a group —$OR_4$, $R_4$ being an aromatic group containing one or two rings, optionally substituted with one or more nitro or halogen radicals. $R_4$ is preferably a 1-benzotriazolyl group, $R_8$ being an alkyl group having from 1 to 6 carbon atoms, optionally substituted with a hydroxyl, a thioalkyl group having from one to six carbon atoms in the alkyl group or a carboxyl or carbonylamido group, an aryl group containing one or two rings, optionally substituted with a hydroxyl, in particular phenyl or benzyl an aralkyl group having one or two aromatic rings and in which the alkyl portion contains from one to six carbon atoms, optionally substituted on the ring with one or more halogen, hydroxy or methoxy groups a five- or six-membered heterocycle having one or two hetero atoms chosen from nitrogen, oxygen and sulphur a 3-indolylmethyl group a 4-imidazolylmethyl group. $R_8$ will preferably be an isobutyl group and the amino acid will belong to the L series, $R_9$ being a group which is readily removable to regenerate the free amine, and can be an oxycarbonyl radical of the structure A—O—CO—, in which A is an alkyl group containing from one to six carbon atoms, or an aryl group, optionally substituted with one or more methoxy, halogen or nitro groups, for example benzyl, p-chlorobenzyl, p-bromobenzyl, p-nitrobenzyl, 9-fluorenylmethyl, p-methoxybenzyl, 2,4-dichlorobenzyl, 2,6-dichlorobenzyl, tert-amyl, isopropyl, adamantyl an alkanoyl or alkenyl group containing from one to six carbon atoms or an aroyl group, such as formyl, trifluoracetyl, phthalyl p-toluenesulphonyl p-nitrosulphenyl, $R_9$ will preferably be a tert-butyloxycarbonyl group.

This condensation is performed as described above, to convert a compound of formula (V) to a compound of formula (I). A compound possessing the general formula (VII) is obtained. This compound is deprotected to obtain the free amine of formula (VIII). This deprotection may be carried out by hydrolysis either in an acid medium, in the presence of a strong organic or inorganic acid such as hydrochloric acid, sulphuric acid, hydrofluoric acid, hydrobromic acid, a sulphonic acid such as, for example, paratoluenesulphonic acid or methanesulphonic acid, acetic acid optionally substituted with one to three chlorine or fluorine atoms, formic acid or any other suitable acid, in a solvent or a mixture of aqueous or organic solvents such as a carboxylic acid, a halogenated aliphatic hydrocarbon, an aromatic hydrocarbon optionally substituted with a halogen or hydroxy group, an aliphatic alcohol optionally substituted with one or more halogen atoms such as, for example, ethanol or trifluoroethanol, or alternatively a linear or cyclic aliphatic ether such as, for example, 1,2-dimethoxyethane, dioxan or tetrahydrofuran. The preferred method of hydrolysis consists in dissolving the compound in a solution containing approximately 10% of trifluoroacetic acid in methylene chloride, and in stirring for a period of a few minutes to a few hours at a temperature of between zero degrees centigrade and the refluxing temperature of the reaction mixture, or in a basic medium in some cases, such as, for example, when the protective group $R_9$ is OCOA and A is a 9-fluorenylmethyl group, the solvent used being a solvent or a mixture of aqueous or organic solvents such as a halogenated aliphatic hydrocarbon, aprotic or aprotic dipolar solvent such as, for example, dimethylformamide, dimethyl sulphoxide, tetramethylene sulphone (sulpholane), N-methylpyrrolidone, acetonitrile or N,N-dimethylacetamide; an aliphatic alcohol, an ester of an aliphatic alcohol with a carboxylic acid, a linear or cyclic ether; it being possible for the basic agent to be an inorganic base such as an alkali metal hydroxide or organic hydroxide, such as an aliphatic tertiary amine such as, for example, triethylamine, diisopropylethylamine, N-methylpyrrolidone or alternatively N-methylmorpholine, or alternatively by catalytic hydrogenation, it being possible for the catalyst used to be a noble metal such as, for example, palladium, or alternatively an oxide of one of these metals deposited on a support; the nature of the appropriate catalyst varying with the nature of the group $R_9$; when $R_9$ is an AOCO and A is benzyl, the catalyst can be palladium on charcoal.

The amino acid derivative obtained, of formula (VIII), is separated into its diastereoisomers by chromatography to give the two isomers of the amine of formula (VIII).

By Edman degradation, the two enantiomers, (R) and (S), of the amine (V) are recovered.

The Edman degradation consists in reacting an aryl isothiocyanate of formula $R_{10}$—N=C=S with the optically active free amine of formula (VIII) to obtain the thiourea of formula (IX); the group $R_{10}$ being an aryl radical such as phenyl or naphthyl, optionally substituted with one or more substituents chosen from halogens, a methoxy group or a lower alkyl group having from one to six carbon atoms. The reaction is performed in a solvent which cannot react with the isothiocyanate group, such as a halogenated aliphatic hydrocarbon, an aromatic hydrocarbon optionally substituted with a halogen group, an aliphatic ester of an aliphatic alcohol, an aprotic dipolar solvent such as, for example, dimethylformamide, dimethyl sulphoxide, tetramethylene sulphone (sulpholane) N-methylpyrrolidone, acetonitrile or N,N-dimethylacetamide, or alternatively a linear cyclic aliphatic ether such as, for example, dioxan or tetrahydrofuran. Usually, it is preferable to perform this reaction in methylene chloride, at a temperature of between zero degrees and the refluxing temperature of the reaction mixture, the reaction being complete after a period of time between a few minutes and a few hours.

then cyclizing and cleaving the thiourea obtained of formula (IX), to give the optically active amine (V). This may be carried out in one or two stages, but it is usually preferable to carry out both stages without isolating the intermediate cyclic compound, thereby avoiding a purification. The procedure is generally performed by dissolving the thiourea in 5 to 100 volumes of a solution having a concentration of between 5 and 100 percent of a strong acid such as, for example, trifluroacetic acid, in an organic solvent such as, for example, a halogenated hydrocarbon, preferably methylene chloride, and by stirring this solution at a temperature of between 0° and the refluxing temperature of the reaction mixture, for a period between a few minutes and a few hours.

The separation of the isomers of the amine of (V) may also be carried out by salification, crystallization and infiltration of the salt obtained. The process consists in dissolving the racemic amine of formula (V) in a solution of an optically active acid known for separating organic basis, such as, for example, mandelic acid, dibenzoyl tartaric acid, di-(p-toluoyl) tartaric acid, camphor sulphonic acid, p-nitrobenzoyl glutamic acid, tartaric acid, binaphthylphosphoric acid, in an aqueous or organic solvent such as, for example, a lower aliphatic alcohol, acetone, acetonitrile or any other solvent in which only one of the two diastereoisomeric salts recrystallizes.

It is preferable to employ L-tartaric acid or (+)—binaphylphosphoric acid, an acetone or acetone nitrile as a solvent.

The intermediate products of formula (XI):

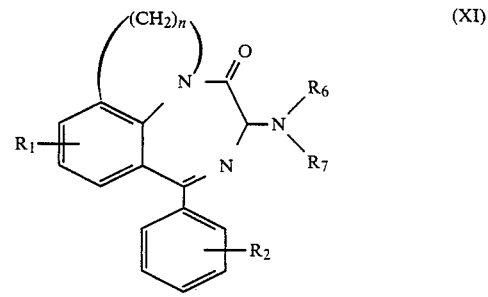

n, $R_1$ and $R_2$ having the meanings stated in Claim 1, $R_6$ being hydroxy when $R_7$ denotes an additional bond between the nitrogen atom bearing a $R_6$ and the diazepine ring and $R_6$ being hydrogen when $R_7$ is hydrogen, are useful intermediates for the preparation of the active products according to the invention.

The invention also relates to a medicinal product for combating gastrointestinal disorders and disorders of the pancreas and the gall bladder, disorders of the central nervous system and pain, characterized in that it comprises a benzodiazepine according to the invention.

The examples which follow illustrate the invention.

Except where otherwise stated, the methods used during the synthesis and analyses are as follows:

The melting points were measured in a capillary tube on a Mettler apparatus, and were not corrected. The nuclear magnetic resonance spectrum were recorded on a JEOL FX-90Q spectrometer (90 MHz), tetramethylsilane being used as an internal reference. The spectra are described in the following manner: chemical shift (expressed in ppm relative to the internal reference), multiplicity, extent of integration, coupling constant where appropriate and assignment. The infrared spectra were recorded in a potassium bromide disk on a Shimadzu IR-435 spectrometer. Flash chromotography was performed as described by Still on silicagel (E. MERCK ITEM 4063) [Still W. C., Kahn M. Mitra A., J. Org. Chem. (1978), 43, 293]. Thin-layer chromotography was performed on 60F$_{254}$ silica plates 0.25 mm thick (E. Merck 5714). The plates were examined under ultraviolet light or visualized with iodine, Dragendorff's reagent or toluidine reagent. High pressure chromotography (HPLC) was performed on a Jobin-Yvon apparatus.

EXAMPLE 1

4-(indol-2-ylcarbonylamino)-phenyl-6-tetrahydro-1,2,3,4-pyrrolo[3,2,1-jk][1,4]benzodiazepin-3-one Formula I: Ar=2-Indolyl, X=Y=Hydrogen. (Ia):
Stage (a): conversion of a compound of formula (III) to a compound of (IV).

A solution of 6-phenyl-1,2,3,4-tetrahydropyrrolo[3,2,1-jk] [1,4]benzodiazepin-3-one (26.3 g; 0.10 mol) in a mixture of anhydrous toluene (500 ml) and anhydrous tetrahydrofuran (250 ml) is introduced into a three-necked round-bottom flask maintained under a nitrogen atmosphere. The solution is cooled to −20° C. and anhydrous potassium tert-butylate (37.1 g; 0.33 mol) is added thereto; solution becomes dark red-brown. After 30 minutes' stirring at −20° C., isoamyl nitrite (20.1 ml; 0.15 mol) is added and the mixture is allowed to return to room temperature, at which it is stirred for 30 minutes. A solution of acetic acid (50 ml) in water (500 ml) is then added. The organic phase is separated after settling has taken place, and the aqueous phase is re-extracted with methylenechloride (3×200 ml). The combined organic extracts are evaporated under reduced pressure and the residue is purified by flash chromatography on a silica column, the eluent used being a mixture of increasing polarity of acetone in methylene chloride. 23.3 g of 4-hydroxyimino-6-phenyl-1,2,3,4-tetrahydro pyrrolo[3,2,1-jk] [1,4]benzodiazepin-3-one are thereby obtained in the form of a yellow solid (80% yield). Melting point: 215° C. (decomposition).

Nuclearmagnetic resonance spectrum.

| 11.20 ppm s | 1 proton | | OH |
|---|---|---|---|
| 7.80–7.00 ppm m | 8 protons | | aromatic |
| 4.35 ppm t | 2 protons | J = 8 Hz | $CH_2$—N |
| 3.20 ppm t | 2 protons | J = 8 Hz | $CH_2$ benzyl |

Infrared spectrum
Bands at 3300, 3050, 2800, 1665, 1620, 1600, 1570, 1525, 1515, 1340, 1215, 1150 and 1010–950 cm$^{-1}$.

Stage (b): conversion of a compound of formula (IV) to a compound of formula (V).
1st method A suspension of Raney nickel (100 g) and oxime of stage 1a (23.2 g) in methanol (1000 ml) is introduced into a three-necked round-bottom flask connected to a hydrogen reservoir maintained at a pressure slightly above atmospheric pressure. The suspension is stirred at room temperature until the absorption of hydrogen is complete (approximately 20 hours). The suspension is filtered and washed with five times 200 ml of methanol. The methanol is evaporated off under reduced pressure, to give a viscous oily residue which is purified by flash chromatography on a silica column, the eluent used being a mixture of increasing polarity of acetone in methylene chloride. 11 g of 4-amino-6-phenyl-1,2,3,4-tetrahydropyrrolo [3,2,1-jk] [1,4]benzodiazepin-3-one (58% yield) are thereby obtained in the form of an oil, which is employed immediately in the following reaction.

The nuclearmagnetic resonance spectrum

| 7.65–7.00 ppm m | 8 protons | aromatic |
|---|---|---|
| 4.80–4.20 ppm m | 2 protons | $CH_2$—N |
| 4.20–3.60 ppm m | 3 protons | CH—$NH_2$ |
| 3.40–2.80 ppm m | 2 protons | $CH_2Ar$ |

2nd method
9.6 g of ruthenium on charcoal (5% ruthenium) are introduced under nitrogen into a reactor capable of withstanding a pressure of 12 bars. The ruthenium is hydrogenated for 2 hours at 20° C. under 10 bars of hydrogen. 32 g (110 mmol) of 4-hydroxyimino-6-phenyl-1,2,3,4-tetrahydropyrrolo[3,2,1-jk][1,4]benzodiazepin-3-one are added under a nitrogen atmosphere. The reactor is again brought to a hydrogen pressure of 8 bars, and heated gradually to 72° C. in the course of two hours. This temperature is maintained for a further hour. The mixture is cooled and filtered on silica, rinsing with methanol. After chromatography on silica in methylene chloride enriched with acetone, 29 g (yield: 94%) of 4-amino-6-phenyl-1,2,3,4-tetrahydropyrrolo [3,2,1-jk] [1,4]benzodiazepine-3-one are obtained. Formula (V), n=2, $R_1$=H, $R_2$=H; (Va). TLC: $H_2CCl_2$/MeOH 95:5 Rf=0.2
NMR:

| 7.65–7.0 ppm | 8 protons | aromatic |
|---|---|---|
| 4.80–4.20 ppm | 2 protons | $CH_2$H |
| 4.20–3.60 ppm | 3 protons | CH—$CH_2$ |
| 3.40–2.80 ppm | 2 protons | $CH_2Ar$ |

IR: 3350, 1675, 1600, 1560, 1440, 1340, 1240, 1100, 730, 690 cm$^{-1}$.

Stage (1c): conversion of a compound of formula (V) to a compound of formula (I).

A solution of the amine prepared in 1b (11.0 g; 39.7 mmole) in anhydrous methylene chloride (200 ml) is introduced into a dry round-bottom flask maintained protected from moisture by a calcium chloride guard tube and protected from oxygen by a stream of nitrogen. 2-Indolylcarboxylic acid chloride (7.12 g; 39.6 mmole) is added thereto. The mixture is stirred at ambient temperature and triethylamine (4.01 g, 39.6 mmole) is added dropwise thereto.

The progress of the reaction is followed by thin-layer chromatography. After the starting material has disappeared (approximately one hour's reaction), the reaction medium is diluted with methylenechloride (200 ml) and washed successively with normal hydrochloric acid (200 ml), saturated sodium bicarbonate solution (200 ml), and water (200 ml). The organic phase is then evaporated under reduced pressure and the residue purified by a flash chromatography on a silica column, the element used being a mixture of increasing polarity of acetone in methylene chloride. 12.6 g (75.5%) of the compound (Ia) are thereby obtained in the form of a white solid. Melting point 218° C.

Nuclear magnetic resonance spectrum (recorded on a Brücker spectrometer at 250 MHz).

| | | | |
|---|---|---|---|
| 11.66 ppm s | 1 proton | | indole NH |
| 9.58 ppm d | 1 proton | J = 8 Hz | amide NH |
| 7.65 ppm m | 2 protons | | aromatics H |
| 7.50 ppm m | 6 protons | | aromatics H |
| 7.20 ppm m | 4 protons | | aromatics H |
| 7.06 ppm m | 1 proton | J = 7 Hz | aromatic H |
| 5.55 ppm d | 1 proton | J = 8 Hz | CH—NH |
| 4.51 ppm m | 1 proton | | $CH_2$—N |
| 3.96 ppm m | 1 proton | | $CH_2$—N |
| 3.41 ppm m | 1 proton | | benzyl $CH_2$ |
| 3.34 ppm m | 1 proton | | benzyl $CH_2$ |

Infra-red spectrum.
Bands at 3300, 3260, 3040, 2800, 1660, 1635, 1600, 1530, 1395, 1340, 1300, 1250 and 1210 cm$^{-1}$.

EXAMPLE 2

4-(4-Chlorobenzoylamino)-6-phenyl-1,2,3,4-tetrahydropyrrolo-[3,2,1-jk]benzodiazepin[1,4]-3-one Formula I; Ar=4-chlorophenyl, X=Y=hydrogen, n=2 (Ib):

This compound is prepared from the amine prepared in Example 1, Stage (b), in the following manner:

A solution of the amine prepared in Example 1 Stage (b) (4.7 g; 16.9 mmol) in anhydrous methylene chloride (100 ml) is introduced into a dry round-bottomed flask maintained protected from moisture by a calcium chloride guard tube. para-Chlorobenzoic acid chloride (2.97 g, 17.0 mmol) is added thereto. The mixture is stirred at room temperature and triethylamine (1.72 g; 17.0 mmol) is added dropwise thereto. The progress of the reaction is followed by thin-layer chromatography. After the starting material has disappeared (approximately 1 hour's reaction), the reaction medium is diluted with methylene chloride (200 ml) and washed successively with normal hydrochloric acid (100 ml), saturated sodium bicarbonate solution (100 ml), saturated sodium bicarbonate solution (100 ml) and water (100 ml). The organic phase is then evaporated under reduced pressure and the residue is purified by flash chromatography on a silica column, the eluant used being a mixture of increasing polarity of acetone in methylene chloride. 5.7 g (81% yield) of the compound Ib are thereby obtained in the form of a white solid. Melting point: 215° C. (decomposition). TLC: $H_2CCl_2$/acetone 95:5 Rf=0.64.

Nuclear magnetic resonance spectrum:

| | | | |
|---|---|---|---|
| 8.08 ppm d | 1 proton | J = 8 Hz | CH—NH—CO |
| 7.96 ppm m | 2 protons | | aromatic H |
| 7.70-7.00 ppm m | 10 protons | | aromatic H |
| 5.60 ppm d | 1 proton | J = 8 Hz | CH—NH—CO |
| 4.80-4.50 ppm m | 1 proton | | $CH_2$—N |
| 4.30-3.70 ppm m | 1 proton | | $CH_2$—N |
| 3.60-2.80 ppm m | 2 protons | | benzyl $CH_2$ |

Infra-red spectrum:
Bands at 3300, 3050, 2900, 1690, 1650, 1590, 1565, 1530, 1490, 1440, 1385, 1340, 1270, 1130, 1080 and 1000 cm$^{-1}$.

EXAMPLE 3

4-(3-Iodobenzoylamino)-6-phenyl-1,2,3,4-pyrrolo[3,2,1-j,k][1,4]benzodiazepin-3-one Formula I; Ar=3-Iodophenyl, X=Y=hydrogen (Ic):

This compound is prepared from the amine prepared in Example 1 Stage (b), in the following manner:

A solution of the amine (3 g; 10.8 mmol) in anhydrous methylene chloride (100 ml) is introduced into a dry round-bottomed flask maintained protected from moisture by calcium chloride guard tube. meta-Iodobenzoic acid chloride (3.14 g; 11.8 mmol) is added thereto. The mixture is stirred at room temperature and triethylamine (1.20 g; 11.9 mmol) is added dropwise thereto. The progress of the reaction is followed by thin-layer chromatography. After the starting material has disappeared (approximately 1 hour's reaction), the reaction medium is diluted with methylene chloride (200 ml) and washed successively with normal hydrochloric acid (100 ml), saturated sodium bicarbonate solution (100 ml) and water (100 ml). The organic phase is then evaporated under reduced pressure and the residue is purified by flash chromatography on a silica column, the eluant used being a mixture of increasing polarity of acetone in methylene chloride. 4.0 g (73% yield) of the compound Ic are thereby obtained in the form of a white solid. Melting point: 258° C. TLC: $H_2CCl_2$/acetone 95:5 Rf=0.55.

Nuclear magnetic resonance spectrum:

| | | | |
|---|---|---|---|
| 9.70 ppm d | 1 proton | J = 8 Hz | CH—NH—CO |
| 8.46 ppm s | 1 proton | | aromatic H |
| 8.30-7.80 ppm m | 3 protons | | aromatic H |
| 7.70-7.10 ppm m | 8 protons | | aromatic H |
| 5.50 ppm d | 1 proton | J = 8 Hz | CH—NH—CO |
| 4.70-4.40 ppm m | 1 proton | | $CH_2$—N |
| 4.10-3.70 ppm m | 1 proton | | $CH_2$—N |
| 3.60-3.00 ppm m | 2 protons | | benzyl $CH_2$ |

Infra-red spectrum:
Bands at 3200, 3050, 3000, 1685, 1640, 1600, 1560, 1520, 1465, 1440, 1430, 1380, 1340, 1285, 1210 and 1190 cm$^{-1}$.

EXAMPLE 4

6-Phenyl-4-(3,4,5-trimethoxybenzoylamino)-1,2,3,4-tetrahydropyrrolo[3,2,1-jk][1,4]benzodiazepin-3-one Formula (I); Ar=3,4,5-trimethoxyphenyl, $R_1=R_2$=hydrogen, n=2. (Id).

This compound is prepared from 5 g (18 mmol) of the amine described in Example 1 Stage (b), in the same manner as in Example 2 Stage (c), from 3.97 g (18 mmol) of 3,4,5-trimethoxybenzoic acid chloride and 1.8 g (18 mmol) of triethylamine in 200 ml of methylene chloride. After chromatography, 8 g (94%) of the compound (Id) are obtained, a white solid crystallizing in the form of a solvate containing a third of a molecule of water. M.p. 158° C.

NMR:

| | | | |
|---|---|---|---|
| 8.0 ppm d | 1 proton | J = 8 Hz | CH—NH—CO |
| 7.60-7.0 ppm m | 10 protons | | aromatic |
| 5.62 ppm d | 1 proton | J = 8 Hz | CH—NH—CO |
| 4.55 ppm m | 1 proton | | $CH_2N$ |
| 4.15-3.75 ppm m | 1 proton | | $CH_2N$ |
| 3.90 ppm s | 9 protons | | $CH_2O$ |
| 3.25 ppm m | 2 protons | | $CH_2Ar$ |

IR: 3320, 2950, 1680, 1640, 1530, 1495, 1310, 1250, 1120, 1000, 760, 730, 700 cm$^{-1}$.

EXAMPLE 5

Preparation of (−)-(4S) and (+)-(4R)-4-(2-indolylcarbonylamino)-6-phenyl-1,2,3,4-tetrahydropyrrolo[3,2,1-jk][1,4]benzodiazepin-3-one Formula (I): Ar=2-indolyl; $R_1=R_2=H$; n=2; (Ie)-laevorotatory isomer and (If)-dextrorotatory isomer.

Stage (a)

Preparation of 6-phenyl-4-[N-(N-tert-butyloxycarbonyl-L-leucyl)amino]-1,2,3,4-tetrahydropyrrolo[3,2,1-jk][1,4]benzodiazepin-3-one.

Formula (VII); $R_1=R_2=H$: n=2; $R_8$=isobutyl; $R_9$=tert-butyloxycarbonyl.

19 g (68.5 mmol) of the amine prepared in Example 1 stage (b) are dissolved at 5° C. in 500 ml of methylene chloride in a three-necked round-bottomed flask equipped with a calcium chloride guard tube, a dipping thermometer and a nitrogen inlet. 17.1 g (68.5 mmol) of Boc-L-leucine hydrate and 10.5 g (68.5 mmol) of 1-hydroxybenzotriazole hydrate are added. The solution of 500 ml of methylene chloride containing 14.1 g (68.5 mmol) of 1-hydroxybenzotriazole hydrate are added. The solution of 500 ml of methylene chloride containing 14.1 g (68.5 mmol) of dicyclohexylcarbodiimide are then added dropwise. The mixture is stirred for 2 hours at 5° C. and allowed to return to room temperature. After 20 h, the insoluble matter is filtered off and rinsed copiously with methylene chloride. After evaporation, the residue is chromatographed on a silica column, eluting with methylene chloride and rinsed with acetone. Obtained: 32.5 g (97%); TLC: $H_2CCl_2$/acetone 5% Rf=0.8.

NMR:

| | | | |
|---|---|---|---|
| 7.75 ppm d | 1 proton | J = 8 Hz | CH—NH—CO |
| 7.60–6.90 ppm m | 8 protons | | aromatic |
| 5.42 ppm d | 1 proton | J = 8 Hz | CH—NH—CO |
| 5.10 ppm d | 1 proton | | NH—CH—CO |
| 4.60 ppm m | 1 proton | | $CH_2N$ |
| 3.95 ppm m | 1 proton | | $CH_2N$ |
| 3.70–1.70 ppm m | 3 protons | | $CH_2N$,NH—CH—CO |
| 3.25 ppm m | 2 protons | | $CH_2Ar$ |
| 1.90–1.20 ppm m | 3 protons | | $CHCH_2$ |
| 1.45 ppm s | 9 protons | | $C(CH_3)$ |
| 1.0 ppm d | 6 protons | | $(CH_3)_2$ |

IR: 3300, 2900, 1710–1650, 1500, 1440, 1160, 1020 cm$^{-1}$.

Stage (b)

Preparation of 4-[N-(L-leucyl)amino]-6-phenyl-1,2,3,4-tetrahydropyrrolo[3,2,1-jk][1,4]benzodiazepin-3-one.

Formula (VIII): $R_1=R_2=H$; $R_8$=isobutyl; n=2.

32.5 g (66 mmol) of the product of the above stage are dissolved in 300 ml of methylene chloride. The mixture is cooled in ice, and 300 ml of trifluoroacetic acid are added in the course of one minute but without allowing the temperature to rise above 5° C. After ½ h of stirring, the mixture is evaporated to dryness. The residue is taken up with ethyl acetate and normal sodium hydroxide, and then with water saturated with sodium chloride. The product is dried and evaporated. It is chromatographed on silica, eluting with a mixture of increasing polarity of methanol in methylene chloride. Obtained: 24 g (72%).

To obtain the base:

25 g of salt (trifluoroacetate; 50 mmol) are stirred vigorously with 200 ml of normal sodium hydroxide and 200 ml of ethyl acetate. Settling is allowed to take place, the sodium hydroxide is extracted with 50 ml of ethyl acetate and the ethyl acetate is washed with 50 ml of saturated aqueous sodium chloride solution. The product is dried and evaporated: 19 g (97%).

TLC: AcOEt/MeOH 90:10 Rf=0.3;0.4 (2 spots, corresponding to the 2 diastereoisomers).

NMR:

| | | |
|---|---|---|
| 8.72 ppm d | 1 proton | CH—NH—CO |
| 7.60–6.90 ppm m | 8 protons | aromatic |
| 5.42 ppm d | 1 proton | CH—NH—CO |
| 4.40 ppm m | 1 proton | $CH_2N$ |
| 3.95 ppm m | 1 proton | $CH_2N$ |
| 3.60–3.0 ppm m | 3 protons | CO—CH—NH, $CH_2Ar$ |
| 2.0–1.20 ppm m | 3 protons | $CHCH_2$ |
| 1.70 ppm s | 2 protons | $NH_2$ |
| 0.95 ppm m | 6 protons | $(CH_3)_2$ |

IR: 3350, 2950, 1660, 1600, 1440, 1380, 1240 cm$^{-1}$.

Stage (c)

Separation of the optical isomers.

A flash chromatography device is set up with 400 g of silica in a column 5 cm in diameter. The product is dissolved in ethyl acetate and eluted successively with pure ethyl acetate (2.5 l), ethyl acetate containing 5% of methanol (2.5 l), ethyl acetate containing 10 ml of methanol (2.5 l) and ethyl acetate containing 20% of methanol (2.5 l); the eluates are examined on silica plates, and indentical fractions are combined and evaporated.

The following are collected:
fractions 8/14 good product, isomer A, 11.5 g
fractions 15,16,17 mixture of isomers, 0.4 g
fractions 18/27 isomer B, 11.5 g Separation yield: 96% (48% of each of the two isomers).

Isomer A: TLC: AcOEt/MeOH 90:10 Rf=0.5
$[\alpha D]=-91°5(c=1.0/H_2CCl_2)$
Isomer B: TLC: AcOEt/MeOH 90:10 Rf=0.3
$[\alpha D]=+56°3(c=1.0/H_2CCl_2)$ Stage (d)

Preparation of 6-phenyl-4-[N-(N-phenylthioureido-L-leucyl)amino]-1,2,3,4-tetrahydropyrrolo[3,2,1-jk][1,4]benzodiazepin-3-one.

Formula (IX); $R_1=R_2=H$; $R_8$=isobutyl; $R_{10}$=phenyl; n=2; isomer A.

4.05 g (30 mmol) of phenyl isocyanate are added dropwise to a stirred solution of 200 ml of methylene chloride containing 11.7 g (30 mmol) of the isomer A of the preceding stage. The process of the reaction is followed on plates. After one hour, the solvent is evaporated off. The residue (15.5 g) is taken up with methylene chloride containing 10% of ethyl acetate and chromatographed on silica in methylene chloride enriched with ethyl acetate. The solvent is evaporated from the fractions containing the product. Obtained: 15 g (95%). TLC: $H_2CCl_2$/AcOEt 85:15 Rf=0.4.

Stage (e)

(−)-(4S)-4-Amino-6-phenyl-1,2,3,4-tetrahydropyrrolo[3,2,1-jk][1,4]benzodiazepin-3-one.

Formula (Va); laevorotatory isomer.

5.8 g (30 mmol) of 6-phenyl-4[N-(N-phenylthioureido)-L-leucy)amino]-1,2,3,4-tetrahydropyrrolo[3,2,1-jk][1,4]benzodiazepin-3-one, obtained in Stage (d), are dissolved in 200 ml of trifluoroacetic acid, stirring at room temperature. The mixture is heated for one hour at 40° C. and evaporated. Methylene chloride is driven off several times in order to remove the excess trifluoroacetic acid. The product is chromatographed on silica, eluting with ethyl acetate gradually enriched with methanol. 8 g (68%) of white needles of (−)-(4S)-4-amino-6-phenyl-1,2,3,4-tetrahydropyrrolo[3,2,1-jk][1,4]benzodiazepin-3-one trifluoroacetate are obtained. TLC: H₂CCl₂/AcOEt 85:15 Rf=0.4.
NMR:

| | | |
|---|---|---|
| 7.60–6.90 ppm m | 8 protons | aromatic |
| 4.65 ppm m | 1 proton | CH₂N |
| 4.45 ppm s | 1 proton | CHNH₃ |
| 3.90 ppm m | 1 proton | CH₂N |
| 3.50–2.90 ppm m | 5 protons | NH₃,CH₂Ar |

Stage (f)
(−)-(4S)-4-(2-Indolylcarbonylamido)-6-phenyl-1,2,3,4-tetrahydropyrrolo[3,2,1-jk][1,4]benzodiazepin-3-one.

Formula (Ie) laevorotatory isomer.

The solution of 11 g of 1-(S)-4-amino-phenyl-1,2,3,4-tetrahydropyrrolo[3,2,1-jk][1,4]benzodiazepin-3-one (39.7 mmol) in 200 ml of anhydrous methylene chloride is introduced into a dry round-bottomed flask maintained protected from moisture by a calcium chloride guard tube, and protected from oxygen by a stream of nitrogen. 7.12 g (59.6 mmol) of 2-indolylcarboxylic acid chloride are added and the mixture is stirred at room temperature. Pyridine (3.13 g; 39.6 mmol) is added dropwise; the progress of the reaction is followed by thin-layer chromatography.

After the starting material has disappeared (approximately one hour's reaction), the reaction medium is diluted with methylene chloride (200 ml) and washed successively with normal hydrochloric acid (200 ml), saturated sodium bicarbonate solution (200 ml) and water (200 ml). The organic phase is dried and evaporated under reduced pressure, and the residue is purified by chromatography on a silica column, the eluant used being a mixture of increasing polarity of acetone in ethyl acetate. 12.6 g (75.5%) of white solid are obtained. Mp. 206° C. [αD]=−56°(H₂CCl₂). TLC: H₂CCl₂/acetone 95:5 Rf=0.5.
NMR:

| | | | |
|---|---|---|---|
| 11.6 ppm s | 1 proton | | indole NH |
| 9.58 ppm d | 1 proton | J = 8 Hz | CH—NH—CO |
| 7.65–7.06 ppm m | 13 protons | | aromatic |
| 5.55 ppm d | 1 proton | J = 8 Hz | CH—NH—CO |
| 4.51 ppm m | 1 proton | | CH₂N |
| 3.96 ppm m | 1 proton | | CH₂N |
| 3.41 m | 1 proton | | CH₂Ar |
| 3.34 m | 1 proton | | CH₂Ar |

IR: 3300, 3260, 3040, 2800, 1660, 1635, 1600, 1530, 1395, 1340, 1300, 1250, 1210 cm⁻¹.

Stage (g)
Preparation of 6-phenyl-4-[N-(N-phenylthioureido)-L-leucyl)-amino]-1,2,3,4-tetrahydropyrrolo[3,2,1-jk][1,4]benzodiazepin-3-one.

Formula (IX) isomer B.

4.05 g (30 mmol) of phenyl isothiocyanate are added dropwise to a stirred solution of 200 ml of methylene chloride containing 11.7 g (30 mmol) of the isomer B of Stage (c). The progress of the reaction is followed on plates. After one hour, the solvent is evaporated off. The residue (15.5 g) is taken up in methylene chloride containing 10% of ethyl acetate, and chromatographed on silica in methylene chloride enriched with ethyl acetate. The fractions containing the product are combined. Obtained: 15 g (95%). TLC: H₂CCl₂/AcOEt 95:15 Rf=0.4.

Stage (h)
(+)-(4R)-4-Amino-6-phenyl-1,2,3,4-tetrahydropyrrolo[3,2,1-jk][1,4]benzodiazepin-3-one.

Formula (Va); dextrorotary isomer.

5.8 g (30 mmol) of 6-phenyl-4-[N-(N-phenylthioureido)-L-leucy)amino]-1,2,3,4-tetrahydropyrrolo[3,2,1-jk][1,4]benzodiazepin-3-one, obtained in Stage (g), are dissolved in 200 ml of trifluoroacetic acid, stirring at room temperature. The mixture is heated for one hour at 40° C. and evaporated. The residue is redissolved and then taken to dryness several times in succession to remove the excess trifluoroacetic acid. It is then chromatographed on silica, eluting with ethyl acetate gradually enriched with methanol. 8 g (68%) of white needles of (+)-(4R)-4-amino-6-phenyl-1,2,3,4-tetrahydropyrrolo[3,2,1-jk][1,4]benzodiazepin-3-one trifluoroacetate are obtained. TLC: H₂CCl₂/AcOEt 85:15 Rf=0.4.

Stage (i)
(+)-(4R)-4-(2-Indolylcarbonylamino)-6-phenyl-1,2,3,4-tetrahydropyrrolo[3,2,1-jk][1,4]benzodiazepin-3-one.

Formula (If); dextrorotary isomer.

A solution of 11 g of d-(4R)-4-amino-6-phenyl-1,2,3,4-tetrahydropyrrolo[3,2,1-jk][1,4]benzodiazepin-3-one (39.7 mmol) in 200 ml of methylene chloride is introduced into a dry round-bottomed flask maintained protected from moisture by a calcium chloride guard tube, and protected from oxygen by a stream of nitrogen. 7.12 g (39.6 mmol) of 2-indolecarboxylic acid chloride are added and the mixture is stirred at room temperature. Pyridine (3.13 g; 39.6 mmol) is added dropwise; and the progress of the reaction is followed by thin-layer chromatography.

After the starting material has disappeared (approximately one hour's reaction), the reaction medium is diluted with methylene chloride (200 ml) and washed successively with normal hydrochloric acid (200 ml), saturated sodium bicarbonate solution (200 ml) and water (200 ml). The organic phase is dried and evaporated under reduced pressure, and the residue is purified by chromatography on a silica column, the eluant used being a mixture of increasing polarity of acetone in ethyl acetate. 12.6 g (75.5%) of white solid are obtained. Mp. 306° C. [αD]=+56° (c=1.0/H₂CCl₂). TLC: H₂CCl₂/acetone 95:5 Rf=0.5.

EXAMPLE 6

Preparation of 6-(2-fluorophenyl)-4-(2-indolylcarbonylamino)-1,2,3,4-tetrahydropyrrolo[3,2,1-jk][1,4]benzodiazepin-3-one Formula (I); Ar=2-indolyl; R₁=H; R₂=2-F; n=2; (Ig).

Stage (a)
Preparation of 7-(2-fluorobenzoyl)-indoline/

43.03 g (361 mmol) of indoline are dissolved in 360 ml of tetrachloroethane in a reactor equipped with a central stirrer, a condenser provided with a calcium chloride guard tube, a dipping thermometer, a nitrogen inlet and a pressure-equalizing dropping funnel. The mixture is cooled in an ice bath, and 46.75 g (399 mmol) of boron trichloride, dissolved in 180 ml of tetrachloroethane, are added dropwise, 84 g (694 mmol) of 2-fluoro-benzonitrile are added, followed by 52.2 g (399 mmol) of aluminium trichloride. The mixture is heated for 8 hours at 150°. After being cooled, it is hydrolyzed with 325 ml of 4N-hydrochloric acid. It is heated for a further 20 minutes at 80° C. to complete the hydrolysis. The mixture is allowed to cool and the insoluble matter filtered off. The product is rinsed with ether and dried. The precipitate is taken up with methylene chloride and alkalinized with sodium hydroxide. The organic solution is washed with concentrated sodium chloride solution and dried over sodium sulphate. After filtration and evaporation, 63 g of yellow resin are obtained (yield=72%). TLC: $H_2CCl_2$ Rf=0.5.

NMR:

| 7.50–7.0 ppm | m | 7 protons | aromatic |
|---|---|---|---|
| 6.40 ppm | m | 1 proton | NH |
| 3.80 ppm | t | 2 protons J = 9Hz | $CH_2N$ |
| 3.0 ppm | t | 2 protons J = 9Hz | $CH_2Ar$ |

Stage (b)

117 g (485 mmol) a product of Stage (a) are suspended in 2.5 l of ether in a reactor equipped with a central stirrer, a condenser provided with a calcium chloride guard tube, a dipping thermometer, a nitrogen inlet and a pressure-equalizing dropping funnel. The mixture is cooled to −20° C. and 41 ml (485 mmol) of pyridine are added, followed by 91.6 g (582 mmol) of bromoacetyl chloride added dropwise. The mixture is allowed to return to room temperature and is stirred for 20 h. 2 l of water are added with stirring and the insoluble matter is filtered off. The product is rinsed with water and then hexane, and dried. It is recrystallized in ethyl acetate. 120 g (61% yield) of N-bromoacetyl-7-(2-fluorobenzoyl)indoline are obtained. Mp. 136° C. TLC: $H_2CCl_2$/acetone 95:5 Rf=0.25.

NMR:

| 7.90–6.90 ppm | m | 7 protons | aromatic |
|---|---|---|---|
| 4.20 ppm | t | 2 protons | $CH_2N$ |
| 3.76 ppm | s | 2 protons | $CO-CH_2Br$ |
| 3.20 ppm | t | 2 protons | $CH_2Ar$ |

IR: 1660, 1610, 1450, 1390, 1210, 1100, 1050, 745 $cm^{-1}$.

Stage (c)

1 l of tetrahydrofuran and 570 ml of anhydrous methanol are poured into a reactor equipped with a central stirrer, a condenser provided with a potassium hydroxide guard tube, a dipping thermometer, nitrogen inlet and a pressure-equalizing dropping funnel. After the mixture has been to cooled to −30° C., 320 ml of liquid ammonia are added. 114 g (314 mmol) of product of the preceding stage are then added gradually and the mixture is left stirred until the following day without external cooling. Complete dissolution takes place slowly. After 20 h, the mixture is evaporated to dryness. The residue is washed with water. 140 g of crude product are obtained, and this is chromatographed on silica, eluting with methylene chloride gradually enriched with acetone. 70 g of 6-(2-fluorophenyl)-1,2,3,4-tetrahydropyrrolo[3,2,1-jk][1,4]benzodiazepin-3-one are obtained (79% yield). Mp. 148° C.

Formula (III); n=2; $R_1$=H; $R_2$=2-F; (IIIb).
TLC: $H_2CCl_2$/acetone 95:5 Rf=0.6.

NMR:

| 7.60–6.90 ppm | m | 7 protons | aromatic |
|---|---|---|---|
| 4.40 ppm | s | 2 protons | $CO-CH_2-N$ |
| 4.30 ppm | t | 2 protons | $CH_2N$ |
| 3.20 ppm | t | 2 protons | $CH_2Ar$ |

IR: 1665, 1600, 1445, 1395, 1345, 1210, 740 $cm^{-1}$.

Stage (d)

Preparation of 4-hydroxyimino-6-(2-fluorophenyl)-1,2,3,4-tetrahydro[3,2,1-jk][1,4]benzodiazepin-3-one Formula (IV); n=2; $R_1$=H; $R_2$=2-F; (IVb).

In the same manner as in Example 1 stage (a), starting with 70 g (249 mmol) of the product of the preceding stage, 67 g (87% yield) of a yellow solid are obtained, Mp. 218° C. (dec.). TLC: $H_2CCl_2$/acetone 95:5 Rf=0.29.

NMR:

| 7.80–6.95 ppm | m | 7 protons | aromatic |
|---|---|---|---|
| 4.25 ppm | t | 2 protons | $CH_2N$ |
| 3.40 ppm | s | 3 protons | NOH, $H_2O$ |
| 3.20 ppm | t | 2 protons | $CH_2Ar$ |

IR: 3450, 3120, 3000, 2700, 1620, 1600, 1340, 1300, 1000, 740 $cm^{-1}$.

Stage (e)

Preparation of 4-amino-6-(2-fluorophenyl)-1,2,3,4-hydropyrrolo[3,2,1-jk][1,4]benzodiazepin-3-one.

Formula (V), n=2, $R_1$=H, $R_2$=2-F; (Vb).

1st Method.

In the same manner as in Example 1 Stage (b), 2nd method, starting with 30 g (969 mmol) of the product of the preceding stage, 28 g (98% yield) of a foam is obtained, and this is employed directly in the subsequent reactions. TLC: $H_2CCl_2$/MeOH 95:5 Rf=0.54.

NMR:

| 7.70–6.90 ppm | m | 7 protons | aromatic |
|---|---|---|---|
| 4.45 ppm | m | 1 proton | $CH_2N$ |
| 4.3 ppm | s | 1 proton | $CH-NH_2$ |
| 3.90 ppm | m | 1 proton | $CH_2N$ |
| 3.50–3.10 ppm | m | 2 protons | $CH_2Ar$ |
| 3.20 ppm | s | 2 protons | $NH_2$ |

IR: 3400, 1680, 1580, 1440, 1200, 740 $cm^{-1}$.

2nd Method 5.8 g (168 mmol) of product of stage (d) are suspended in methanol under a nitrogen atmosphere, and 3.99 g (168 mmol) of nickel chloride hexahydrate are added. The mixture is cooled to −20° C. and 1.2 g (336 mmol) of sodium borohydride are added in small amounts. The temperature rises immediately and a black precipitate forms. The mixture is stirred at −20° C. for 30 minutes and evaporated to dryness. The residue is taken up with concentrated hydrochloric acid and the mixture is filtered and alkalinized with concentrated ammonia solution in the presence of methylene chloride. The mixture is evaporated and 6.8 g of crude product are obtained, and this is chromatographed on silica, eluting with methylene chloride gradually enriched with acetone. 2.8 g (48% yield) of a foam identical product obtained by the first method are obtained.

Stage (f)

Preparation of 6-(2-fluorophenyl)-4-(2-indolylcarbonylamino)-1,2,3,4-tetrahydropyrrolo[3,2,1-jk][1,4]benzodiazepin-3-one. (Ig).

In the same manner as Example 1 Stage (c), starting with 5 g (169 mmol) of the product of the preceding stage, 2.6 g (36% yield) of a product whose melting point is 289° C. (decomposition) are obtained after chromatography on silica in a methylene chloride gradient containing acetone. TLC: H$_2$CCl$_2$/acetone 95:5 Rf=0.55.
NMR:

| | | | | |
|---|---|---|---|---|
| 11.65 ppm | s | 1 proton | indole NH |
| 9.58 | d | 1 proton | CH—NH—CO |
| 7.80–6.90 ppm | m | 12 protons | aromatic |
| 5.60 ppm | d | 1 proton | CH—NH—CO |
| 4.50 ppm | m | 1 proton | CH$_2$N |
| 4.0 ppm | m | 1 proton | CH$_2$N |
| 3.30 | m | 2 proton | CH$_2$Ar |

IR: 3250, 1680, 1630, 1525, 1400, 1340, 1300, 1210, 740 cm$^{-1}$

EXAMPLE 7

Preparation of 6-(2-fluorophenyl)-4-[(5-methoxy-2-indolyl)carbonylamino]-1,2,3,4-tetrahydropyrrolo[3,2,1-j,k][1,4]benzodiazepin-3-one Formula (I); Ar=5-methoxy-2-indolyl; R$_1$=H; R$_2$=2-F; n=2; (Ih).

In the same manner as Example 1 Stage (c), starting with 4.25 g (203 mmol) of the product of Example 6 Stage (e). After chromatography on silica in a methylene chloride gradient containing acetone, 4.0 g (42% yield) are obtained. M.p. 214° C. TLC: H$_2$CCl$_2$/acetone 95:5 Rf:0.55
NMR:

| | | | | |
|---|---|---|---|---|
| 11.5 ppm | s | 1 proton | indole NH |
| 9.5 | d | 1 proton | CH—NH—CO |
| 7.70–6.80 ppm | m | 11 protons | aromatic |
| 5.60 ppm | d | 1 proton | CH—NH—CO |
| 4.50 ppm | m | 1 proton | CH$_2$N |
| 4.0 ppm | m | 1 proton | CH$_2$N |
| 3.80 | s | 3 protons | OCH$_3$ |
| 3.50–3.0 ppm | m | 2 protons | CH$_2$Ar |

IR: 3250, 1680, 1630, 1525, 1440, 1395, 1340, 1220, 1100, 740 cm$^{-1}$.

EXAMPLE 8

Preparation of 6-(2-fluorophenyl)-4-(3-indolylcarbonylamino)-1,2,3,4-tetrahydropyrrolo[3,2,1-jk][1,4]benzodiazepin-3-one Formula (I); Ar=3-indolyl; R$_1$=H; R$_2$=2-F; n=2; (Ii).

In the same manner as in Example 1 Stage (c), starting with 4.0 g (135 mmol) of the product of Example 6 Stage (e) and 2.425 g (135 mmol) of 3-indolecarboxylic acid. After chromatography on silica in a methylene chloride gradient containing acetone, 1.8 g (30%) yield are obtained. M.p. 206° C. TLC: H$_2$CCl$_2$/acetone 85:15 Rf:0.35.
NMR:

| | | | | |
|---|---|---|---|---|
| 10.1 ppm | s | 1 proton | indole NH |
| 8.20 | d | 1 proton | CH—NH—CO |
| 8.00–6.90 ppm | m | 12 protons | aromatic |
| 5.80 ppm | d | 1 proton | CH—NH—CO |
| 4.65 ppm | m | 1 proton | CH$_2$N |
| 4.0 ppm | m | 1 proton | CH$_2$N |
| 3.20 | m | 2 proton | CH$_2$Ar |

IR: 3230, 1675, 1630, 1530, 1490, 1200, 740 cm$^{-1}$.

EXAMPLE 9

Preparation of 6-(2-fluorophenyl)-4-(1-naphthylcarbonylamino)-1,2,3,4-tetrahydropyrrolo[3,2,1-jk][1,4]benzodiazepin-3-one Formula (II); Ar=1-naphthyl; R$_1$=H; R$_2$=2-F; n=2; (Ij).

In the same manner as in Example 1 Stage (c), starting with 4.0 g (135 mmol) of the product of Example 6 Stage (e) and 2.5 g (175 mmol) of 1-naphthylcarboxylic acid chloride. After chromatography on silica on a methylene chloride gradient containing acetone, 2.5 g (41% yield) are obtained. M.p. 150° C. TLC: H$_2$CCl$_2$/acetone 95:5 Rf=0.75.
NMR:

| | | | | | |
|---|---|---|---|---|---|
| 8.60 | d | 1 proton | J = 8Hz | CH—NH—CO |
| 8.0–6.90 ppm | m | 14 protons | | aromatic |
| 5.80 ppm | d | 1 proton | J = 8Hz | CH—NH—CO |
| 4.70 ppm | m | 1 proton | | CH$_2$N |
| 4.05 ppm | m | 1 proton | | CH$_2$N |
| 3.30 | m | 2 protons | | CH$_2$Ar |

IR: 3400, 1680, 1660, 1480, 1440, 1385, 750 cm$^{-1}$.

EXAMPLE 10

Preparation of 8-chloro-6-(2-fluorophenyl)-4-(2-indolylcarbonylamino)-1,2,3,4-tetrahydropyrrolo[3,2,1-jk][1,4]benzodiazepin-3-one Formula (II); Ar=2-indolyl; R$_1$=8-Cl; R$_2$=2-F; n=2; (Ik).

Stage (a)

Preparation of 5-chloro-7-(2-fluorobenzoyl)indoline.

44 g (182 mmol) of 7-(2-fluorobenzoyl)indoline and 800 ml of methylene chloride are poured into a reactor equipped with a central stirrer, a condenser provided with a calcium chloride guard tube, a dipping thermometer, a nitrogen inlet and a pressure-equalizing dropping funnel. 27.9 g (182 mmol) of N-chlorosuccinimide are added gradually and the mixture is stirred over a warm temperature. The mixture is washed with saturated sodium bicarbonate solution and then with water, dried and evaporated. It is chromatographed on silica, eluting with methylene chloride. 42 g (84% yield) are obtained. The product is obtained in the form of a foam which has no definite melting point. TLC: H$_2$CCl$_2$ Rf=0.70.
NMR:

| | | | |
|---|---|---|---|
| 7.60–7.00 ppm | m | 6 protons | aromatic |
| 6.30 ppm | m | 1 proton | NH |
| 3.85 ppm | m | 2 protons | CH$_2$N |
| 3.10 | m | 2 protons | CH$_2$Ar |

Stage (b)

Preparation of N-bromoacetyl-5-chloro-7-(2-fluorobenzoyl)indoline.

55 g (199 mmol) of product of the preceding stage are treated as Example 6 Stage (b) with 34.46 g (219 mmol) of bromoacetyl bromide. 60 g(76% yield) are obtained. TLC: H$_2$CCl$_2$ Rf=0.25.
NMR:

| | | | |
|---|---|---|---|
| 7.90–6.80 ppm | m | 6 protons | aromatic |

-continued

| | | | | |
|---|---|---|---|---|
| 4.25 ppm | t | 2 proton | CH$_2$N | |
| 3.80 ppm | s | 2 protons | CH$_2$Br | |
| 3.20 ppm | t | 2 protons | CH$_2$Ar | |

Stage (c)

Preparation of 8-chloro-6-(2-fluorophenyl)-1,2,3,4-tetrahydropyrrolo[3,2,1-jk][1,4]benzodiazepin-3-one.

Formula (III); R$_1$=8-Cl; R$_2$=2-F; n=2; (IIIc).

According to Example 6 stage (c), starting with 90 g (226 mmol) of product of the preceding stage, 51 g (65% yield) are obtained after chromatography in a gradient of methylene chloride enriched with acetone. Mp=148° C.

TLC:

| | | | |
|---|---|---|---|
| 7.60–7.00 ppm | m | 6 protons | aromatic |
| 4.45 ppm | s | 2 protons | CO—CH$_2$N |
| 4.32 ppm | t | 2 protons | CH$_2$N |
| 4.20 ppm | t | 2 protons | CH$_2$Ar |

IR: 1660, 1440, 1370, 1340, 1225, 880, 800, 745 cm$^{-1}$.

Stage (d).

Preparation of 8-chloro-6-(2-fluorophenyl)-4-hydroxyimino-1,2,3,4-tetrahydropyrrolo[3,2,1-jk][1,4]benzodiazepin-3-one.

Formula (IV); R$_1$=8-Cl; R$_2$=2-F; n=2; (IVc).

In the same manner as in Example 1 stage (a), starting with 45 g (143 mmol) of the product of the preceding stage, 33 g (67% yield) of a yellow solid are obtained, Mp. 264° C. (dec.). TLC: H$_2$CCl$_2$/acetone 90:10 Rf=0.27.

NMR:

| | | | |
|---|---|---|---|
| 7.85–7.0 ppm | m | 6 protons | aromatic |
| 4.32 ppm | t | 2 protons | CH$_2$N |
| 3.48 ppm | s | 1 proton | NOH |
| 3.28 ppm | t | 2 protons | CH$_2$Ar |

IR: 3300, 1655, 1615, 1580, 1445, 1370, 1340, 1220, 1160, 1020, 850, 740 cm$^{-1}$.

Stage (e)

Preparation of 4-amino-8-chloro-6-(2-fluorophenyl)-1,2,3,4-tetrahydropyrrolo[3,2,1-jk][1,4]benzodiazepin-3-one.

Formula (VI): R$_1$=8-Cl; R$_2$=2-F; n=2; (Vc).

In the same manner as in Example 1 stage (b), 2nd method, starting with 30 g (870 mmol) of the product of the preceding stage, 28 g (98% yield) of a foam are obtained and this is employed directly in the subsequent reactions. TLC: H$_2$CCl$_2$/MeOH 95:5 Rf=0.55.

NMR:

| | | | |
|---|---|---|---|
| 7.70–6.95 ppm | m | 6 protons | aromatic |
| 4.60 ppm | m | 1 proton | CH$_2$N |
| 4.40 ppm | s | 1 proton | CH—NH$_2$ |
| 4.0 ppm | m | 1 proton | CH$_2$N |
| 3.23 ppm | m | 2 protons | CH$_2$Ar |
| 2.50 ppm | s | 2 protons | NH$_2$ |

IR: 3350, 1670, 1610, 1580, 1440, 1335, 1210, 860, 790, 750 cm$^{-1}$.

Stage (f)

Preparation of 8-chloro-6-(2-fluorophenyl)-4-[(2-indolyl)-carbonylamino]-1,2,3,4-tetrahydropyrrolo[3,2,1-jk][1,4]benzodiazepin-3-one (Ik).

In the same manner as in Example 1 stage (c), starting with 3.2 g (97 mmol) of the product of the preceding stage 1.75 g (97 mmol) of 2-indolylcarboxylic acid. After chromatography on silica in a methylene chloride gradient containing acetone, 2.7 g (60% yield) are obtained. Mp=248° C. (decomposition). TLC: H$_2$CCl$_2$/acetone 95:5 Rf=0.37.

NMR:

| | | | | |
|---|---|---|---|---|
| 10 ppm | s | 1 | proton | indolyl NH |
| 8.10 ppm | d | 1 | proton J = 8Hz | CH—NH—CO |
| 7.75–6.90 ppm | m | 11 | protons | aromatic |
| 5.7 ppm | d | 1 | proton J = 8 Hz | CH—NH—CO |
| 4.67 ppm | m | 1 | proton | CH$_2$N |
| 4.55 ppm | m | 1 | proton | CH$_2$N |
| 3.25 ppm | m | 2 | protons | CH$_2$Ar |
| 2.15 ppm | m | 2 | protons | H$_2$O |

IR: 3250, 1680, 1640, 1530, 1480, 1445, 1430, 1100, 795, 740 cm$^{-1}$

EXAMPLE 11

Preparation of 8-chloro-4-[(5-chloro-2-indolyl)carbonylamino]-6-(2-fluorophenyl)-1,2,3,4-tetrahydropyrrolo[3,2,1-jk][1,4]benzodiazepin-3-one Formula (I); Ar=5-chloroindolyl; R$_1$=8-Cl; R$_2$=2-F; n=2; (Il).

In the same manner as in Example 1 stage (c), starting with 5.0 g (152 mmol) of the product of Example 10 stage (e) and 3.25 g (152 mmol) of 5-chloro-2-indolylcarboxylic acid chloride. After chromatography on silica in a methylene chloride gradient containing acetone, 2.7 g (38% yield) of a white solid crystallizing with 0.25 molecule of water are obtained. Mp. 246° C. (decomposition). TLC: H$_2$CCl$_2$/acetone 95:5 Rf=0.4.

NMR:

| | | | | |
|---|---|---|---|---|
| 11.75 ppm | m | 1 | proton | indolyl NH |
| 9.65 ppm | d | 1 | proton J = 8 Hz | CH—NH—CO |
| 7.70–6.90 ppm | m | 10 | protons | aromatic |
| 5.60 ppm | d | 1 | proton J = 8 Hz | CH—NH—CO |
| 4.5 ppm | m | 1 | proton | CH$_2$N |
| 4.0 ppm | m | 1 | proton | CH$_2$N |
| 3.2 ppm | m | 2 | protons | CH$_2$Ar |
| 3.20 ppm | m | 2 | protons | H$_2$O |

IR: 3250, 1640, 1530, 1445, 1340, 1200, 790, 750 cm$^{-1}$.

EXAMPLE 12

Preparation of 8-chloro-4-(3,5-dichlorobenzoylamino)-6-(2-fluorophenyl)-1,2,3,4-tetrahydropyrrolo[3,2,1-jk][1,4]benzodiazepin-3-one Formula (I); Ar=dichloro-3,5-phenyl; R$_1$=8-Cl; R$_2$=2-F; n=2; (Im).

In the same manner as Example 1 stage (c), starting with 5.0 g (152 mmol) of the product of Example 10 stage (e) and 3.42 g (152 mmol) of 3,5-dichlorobenzoic acid chloride. After chromatography on silica on a methylene chloride gradient containing acetone, 4.4 g (58% yield) of a solid crystallizing with 0.25 molecule of water are obtained. Mp=291° C. (decomposition). TLC: H$_2$CCl$_2$/acetone 95:5 Rf=0.45.

NMR: (trifluoroacetic acid):

| | | | |
|---|---|---|---|
| 8.10–7.30 ppm | m | 9 protons | aromatic |

-continued

| | | | | |
|---|---|---|---|---|
| 6.25 ppm | m | 1 | proton | CH—NH—CO |
| 5.0 ppm | m | 1 | proton | $CH_2N$ |
| 4.40 ppm | m | 1 | proton | $CH_2N$ |
| 3.55 ppm | m | 2 | protons | $CH_2Ar$ |

IR: 3250, 3050, 1680, 1640, 1550, 1530, 1470, 1440, 1280, 1200, 865, 800, 750 cm$^{-1}$.

EXAMPLE 13

Preparation of 5-(2-indolylcarbonylamino)-7-phenyl-1,2,3,3a,4,5-hexahydropyrido[3,2,1-jk][1,4]benzodiazepin-4-one Formula (I); Ar=2-indolyl; $R_1$=H; n=3; (In).

Stage (a)

Preparation of 5-hydroxyimino-7-phenyl-1,2,3,3a,4,5-hexahydropyrido[3,2,1-jk][1,4]benzodiazepin-4-one.

Formula (IV); $R_1$=H; $R_2$=H; n=3; (IVd).

In the same manner as in Example 1 stage (a), starting with 26.9 g (97 mmol) of 7-phenyl-1,2,3,4-tetrahydropiperidino[3,2,1-jk][1,4]benzodiazepin-3-one.

After chromatography in a gradient of methylene chloride enriched with acetone, 24.3 g (82% yield) of a solid are obtained, m.p. 195° C. TLC: $H_2CCl_2$/acetone 90:10 Rf=0.3. TLC: $H_2CCl_2$/MeOH 95:5 Rf=0.35.

NMR:

| | | | | |
|---|---|---|---|---|
| 9.20 ppm | s | 1 | proton | NOH |
| 7.90–6.80 ppm | m | 8 | protons | aromatic |
| 4.6 ppm | m | 1 | proton | $CH_2N$ |
| 3.20 ppm | m | 1 | proton | $CH_2N$ |
| 2.95 ppm | m | 2 | protons | $CH_2Ar$ |
| 2.0 ppm | m | 2 | protons | $CH_2—CH_2—CH_2$ |

IR: 3350, 3150, 3050, 1650, 1610, 1440, 1380, 1300, 1000 cm$^{-1}$

Stage (b)

Preparation of 5-amino-7-phenyl-1,2,3,3a,4,5-hexahydropyrido[3,2,1-jk][1,4]benzodiazepin-4-one.

Formula (V); $R_1$=H; $R_2$=H; n=3; (Vd).

In the same manner as Example 1 stage (b), 2nd method, starting with 28.8 g (94 mmol) of product of the preceding stage, after chromatography in a gradient of methylene chloride enriched with acetone, 22 g (80% yield) of a foam not having a definite melting point are obtained, and this is employed directly in the subsequent reactions. TLC: $H_2CCl_2$/10% acetone Rf=0.10 TLC: $H_2CCl_2$/MeOH 95:5 Rf=0.25

NMR:

| | | | | |
|---|---|---|---|---|
| 7.70–7.00 ppm | m | 8 | protons | aromatic |
| 5.0 ppm | m | 2 | protons | CH—$NH_2$, $CH_2N$ |
| 3.30 ppm | m | 1 | proton | $CH_2N$ |
| 2.90 ppm | m | 2 | protons | $CH_2Ar$ |
| 2.62 ppm | s | 2 | protons | $NH_2$ |
| 2.40–1.70 ppm | m | 2 | protons | $CH_2—CH_2—CH_2$ |

IR: 1670, 1590, 1560, 1440, 1300, 1270 cm$^{-1}$.

Stage (c)

In the same manner as Example 1 stage (c), starting with 2.49 g (85 mmol) of the product of the preceding stage, 3.3 g (89% yield) are obtained. Mp. 220° C. TLC: $H_2CCl_2$/MeOH 97:3 Rf=0.75.

NMR:

| | | | | |
|---|---|---|---|---|
| 11.70 ppm | s | 1 | proton | indole NH |
| 9.50 ppm | d | 1 | proton | CH—NH—CO |
| 7.80–7.00 ppm | m | 13 | protons | aromatic |
| 5.68 ppm | d | 1 | proton | CH—NH—CO |
| 4.4 ppm | m | 1 | proton | $CH_2N$ |
| 3.30 ppm | m | 1 | proton | $CH_2N$ |
| 2.95 ppm | m | 2 | protons | $CH_2Ar$ |
| 2.0 ppm | m | 2 | protons | $CH_2—CH_2—CH_2$ |

IR: 3270, 1635, 1530, 1440, 1290, 1250 cm$^{-1}$.

EXAMPLE 14

Preparation of 5-[(5-chloro-2-indolyl)carbonylamino]-7-phenyl-1,2,3,3a,4,5-hexahydropyrido[3,2,1-jk][1,4]benzodiazepin-4-one Formula (I): Ar=5-chloro-2-indolyl; $R_1$=H; $R_2$=H; n=3; (Io).

In the same manner as Example 1 stage (c), starting with 3.2 g (11 mmol) of product of Example 13 stage (b) and 2.35 g (11 mmol) of 5-chloro-2-indolylcarboxylic acid chloride, 4.5 g (89% yield) are obtained. TLC: $H_2CCl_2$/MeOH 97:3 Rf=0.5. $H_2CCl_2$/acetone 95:5 Rf=0.55.

NMR:

| | | | | |
|---|---|---|---|---|
| 11.85 ppm | s | 1 | proton | indole NH |
| 9.60 ppm | d | 1 | proton | CH—NH—CO |
| 7.80–7.10 ppm | m | 12 | protons | aromatic |
| 5.62 ppm | d | 1 | proton | CH—NH—CO |
| 4.35 ppm | m | 1 | proton | $CH_2N$ |
| 3.32 ppm | s | 2 | protons | $H_2O$ |
| 3.20 ppm | m | 1 | proton | $CH_2N$ |
| 2.90 ppm | m | 2 | protons | $CH_2Ar$ |
| 1.95 ppm | m | 2 | proton | $CH_2—CH_2—CH_2$ |

IR: 3380, 3230, 1640, 1530, 1470, 1440, 1390, 760 cm$^{-1}$.

EXAMPLE 15

Preparation of 5-(3-trifluoromethylbenzoylamino)-7-phenyl-1,2,3,3a,4,5-hexahydropyrido[3,2,1-jk][1,4]benzodiazepin-4-one Formula (I); Ar=3-trifluoromethylphenyl; $R_1$H; $R_2$=H; n=3; (Ip).

In the same manner as Example 1 stage (c), starting with 2.91 g (10 mmol) of product of Example 13 stage (b) and 2.08 g (10 mmol) of 3-trifluoromethylbenzoic acid chloride, 4.1 g (88% yield) are obtained. Mp. 250° C. TLC: $H_2CCl_2$/MeOH 97:3 Rf=0.80 $H_2CCl_2$/acetone 95:5 Rf=0.55.

NMR:

| | | | | |
|---|---|---|---|---|
| 10.05 ppm | d | 1 | proton | CH—NH—CO |
| 8.50–7.10 ppm | m | 12 | protons | aromatic |
| 5.65 ppm | d | 1 | proton | CH—NH—CO |
| 4.35 ppm | m | 1 | proton | $CH_2N$ |
| 3.30 ppm | m | 1 | proton | $CH_2N$ |
| 2.95 ppm | m | 2 | protons | $CH_2Ar$ |
| 1.95 ppm | m | 2 | protons | $CH_2—CH_2—CH_2$ |

IR: 3200, 1685, 1650, 1600, 1320, 1260, 1130, 1115 cm$^{-1}$

The results of pharmacological and toxicological studies performed on the benzodiazepines of the invention are given below.

A. In vitro activity

1. The affinity of the compounds of formula (I) for cholecystokinin receptors was studied by determining the 50% inhibitory concentration (IC$_{50}$) for the binding of iodine-125-labelled cholecystokinin (abbreviated below to sulphated [$^{125}$I]-CCK8) to the receptors of rat pancreas plasma membranes (SD50 males, IFFA CREDO, 200-225 g)

of guinea-pig brain membranes (males, COB LABO, 325-350 g) according to the protocol described by INNIS R. B. and SNYDER S. M., Eur. J. Pharmacol., 65, 123-124, 1980.

B. In vivo activity

The antagonist activity of the compounds of formula I for CCK was determined in mice (SWISS male, 18-20 g) on the gastric emptying model described by LOTTI V. J. et al., (LIFE SCIENCES, 39; 1631-1638; 1986), by determining the 50% effective dose (ED$_{50}$) which protects the animals from the inhibition of gastric emptying caused by sulphated CCK-8 (80 μg/kg, sc).

C. Toxicity

The acute toxicity was evaluated and IRWIN's tests (IRWIN S., Psychopharmacologia, 13, 222-257, 1968) were performed in male mice (20-21 g). Table I below shows the results of the tests of binding to the CCK receptors of rat pancreas and of guinea-pig brain, in the form of the 50% inhibitory concentration (IC$_{50}$), as well as, in the last column, the ratio of IC$_{50}$ in respect of the pancreas receptors to the IC$_{50}$ in respect of the brain receptors.

TABLE I

| | Binding (IC$_{50}$) [125I]-CCK8-SO$_4$ | | IC$_{50}$ (brain) / IC$_{50}$ (pancreas) |
|---|---|---|---|
| | Pancreas | Brain | |
| IIa | 11.2 | 847 | 75.6 |
| Ia | 5.3 | 1110 | 209.4 |
| Ib | 37 | 3100 | 83.8 |
| Ic | 45 | 8800 | 195.6 |
| Ie | 1.5 | 477 | 318.0 |
| If | 8640 | 24000 | 2.8 |
| Ig | 0.023 | 366 | 15913 |
| Il | 12.3 | 21392 | 2552.2 |
| Im | 30.6 | 25431 | 831.1 |
| In | 3.9 | 407 | 104.4 |

In the case of (IIa), the ratio of the IC$_{50}$ for the brain receptors of the IC$_{50}$ for the pancreas receptors is equal to 75.6 whereas, in the case of the compounds of formula (I), this ratio is generally much higher. This makes it possible to obtain medicinal products displaying better selectivity for disorders dependent on the peripheral receptors and, as a result, fewer side effects.

Table II below shows the values obtained in the gastric emptying test, the acute toxicity (LD$_{50}$) and also the first dose modifying one of the parameters of behavior studied according to IRWIN's method for the compounds of formula (I), as well as for the compound of formula (+/−)-IIa, which is one of the preferred products described in the patent application cited above. The last column of Table II shows the ratio of the first dose giving rise to the appearance of a symptomatology to the ED$_{50}$ in the gastric emptying test, which is interpreted as a therapeutic index.

TABLE II

| | Gastric emptying ED$_{50}$ mg/kg | Toxicity LD$_{50}$ mg/kg | IRWIN mg/kg | "IRWIN" ED$_{50}$ |
|---|---|---|---|---|
| IIa | 0.050 | >>600 | 120 | 2400 |
| Ia | 0.104 | >>1000 | >1000 | >7600 |
| Ie | 0.087 | >>1000 | >1000 | >11000 |
| Ig | 0.076 | >>1000 | >300 | >3900 |

This index is seen to favor the compounds of the invention, the compound (IIa) causing disorders at a dose of 120 mg/kg upwards, whereas no disorder is observed with the compounds of formula (I) at a dose of 800 or even 1000 mg/kg. In the form of medicinal products, the products of the invention are hence seen to be especially useful in human or veterinary therapy in respect of:

chiefly, cholecystokinin-dependent disorders of the stomach, intestine, pancreas and gallbladder, such as, for example, pancreatitis, disorders of motor function, in particular affecting the stomach or gallbladder, ulcers and irritable colon syndrome;

disturbances of appetite;

pain;

and possibly disorders dependent on the interaction of cholecystokinin with neuromediators of the central nervous system, such as, for example, neuroleptic disorders, Parkinson's disease, psychosis, Gilles de la Tourette's syndrome and tardive dyskinesia.

The products of the invention are administered in the form of compositions suited to the nature and extent of the condition to be treated. The daily dosage in man is usually between 2 milligrams and 1 gram of product, which can be taken in one or more doses. The compositions are prepared in forms compatible with the administration route envisaged, such as, for example, tablets, dragees, capsules, suppositories, gels or suspensions. These compositions are prepared by methods which are familiar to those versed in the art, and comprise from 1 to 60% by weight of active principle (compound of formula I) and 40 to 99% weight of pharmaceutical vehicle suited to and compatible with the active principle and the physical form of the composition envisaged. By way of example, the method of preparation of tablets containing a compound of the invention is given below.

TABLETS

| Formula: | |
|---|---|
| Active substance of formula (I) | 1 to 75 mg |
| Polyvinylpyrrolidone: | 2 mg |
| Carboxymethyl starch: | 8 mg |
| Magnesium stearate: | 3 mg |
| Lactose: | 122 to 76 mg |
| Monocrystalline cellulose: | 60 to 76 mg |
| Per 200 mg tablet. | |

Manufacture:

Dissolve the polyvinylpyrrolidone in the proportion of 0.1 to 1.0% by weight in water, a lower aliphatic alcohol such as, for example, ethanol or an aqueous-alcoholic mixture. Separately, intimately mix the active substance, lactose and half the quantity of cellulose and of carboxymethyl starch, and wet this mixture with the previously prepared solution. Granulate the paste and dry the granules on a screen. Add the remainder of the components of the mixture, then homogenize and tablet on the basis of 200 mg per tablet.

We claim:

1. Benzodiazepines of formula

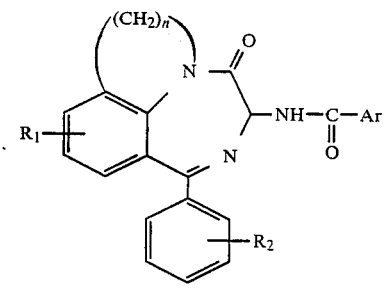

(I)

in which $R_1$ is H or halogen, $R_2$ is H or halogen, Ar is indolyl, phenyl, naphthyl, indolyl monosubstituted with a halogen or with a methoxy or phenyl mono-, di- or trisubstituted with a halogen or with a methoxy or with a trifluoromethyl group, and n is 2 or 3; and their optical isomers.

2. Benzodiazepines according to claim 1, wherein Ar is a 2-indolyl group.

3. Benzodiazepines according to claim 1, wherein $R_2$ is hydrogen or fluorine at the ortho position with respect to the carbon atom linking the phenyl ring to the diazepine ring.

4. Benzodiazepines according to claim 1, wherein $R_1$ is hydrogen or chlorine at the para-position with respect to the nitrogen atom common to the diazepine ring and to the other nitrogen heterocycle fused to the diazepine ring.

5. Benzodiazepines according to claim 1, wherein n is equal to 2.

6. Benzodiazepines according to claim 1, which are:
  (a)  4-(2-indolycarbonylamino)-6-phenyl-1,2,3,4-tetrahydropyrrolo[3,2,1-jk][1,4]benzodiazepin-3-one,
  (b)  6-(2-fluorophenyl)-4-(2-indolylcarbonylamino)-1,2,3,4-tetrahydropyrrolo[3,2,1-jk][1,4]benzodiazepin-3-one,
  (c)  8-chloro-6-(2-fluorophenyl)-4-(2-indolycarbonylamino)-1,2,3,4-tetrahydropyrrolo[3,2,1-jk][1,4]benzodiazepin-3-one, or
  (d)  5-(2-indolycarbonylamino)-7-phenyl-1,2,3,3a,4,5-hexahydropyrido[3,2,1-jk][1,4]benzodiazepin-4-one.

7. Benzodiazepines according to claim 1, wherein an asymmetric carbon atom at the alpha-position with respect to the carbonyl of the diazepine ring possesses the S configuration according to the nomenclature of Cahn, Ingold and Prelog.

8. A medicinal product for combatting gastrointestinal disorders; disorders of the pancreas, gall bladder and appetite; pain; and disorders of the central nervous system, said composition comprising in a pharmaceutically acceptable vehicle in an amount effective to combat said disorders and pain a benzodiazepine having the formula.

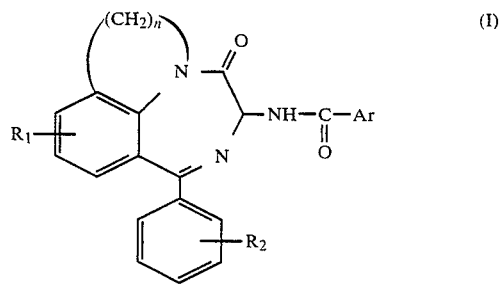

(I)

wherein
  $R_1$ is hydrogen or halogen,
  $R_2$ is hydrogen or halogen,
  Ar is indolyl, phenyl, naphothyl, indolyl monosubstituted with halogen or methoxy, or phenyl mono-, di- or trisubstituted with halogen, methoxy or trifluoromethyl, and
  n is 2 or 3;
  and the optical isomers thereof.

9. The medicinal product of claim 8 wherein said benzodiazapine is present in an amount ranging from 1 to 60 percent by weight and said pharmaceutically acceptable vehicle is present in an amount ranging from 40 to 99 percent by weight.

10. An intermediate having the formula

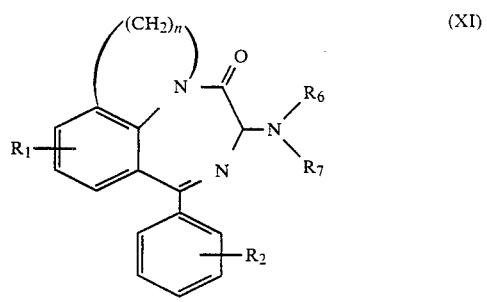

(XI)

wherein
  $R_1$ is hydrogen or halogen,
  $R_2$ is hydrogen or halogen,
  n is 2 or 3,
  $R_6$ is hydroxy when $R_7$ denotes an additional bond between the nitrogen atom bearing $R_6$ and the diazepine ring or
  $R_6$ is hydrogen when $R_7$ is hydrogen.

* * * * *